United States Patent [19]

Ellington et al.

[11] Patent Number: 4,785,661

[45] Date of Patent: Nov. 22, 1988

[54] METHOD FOR ANALYZING SOLVENT EXTRACTED SPONGE CORE

[75] Inventors: William E. Ellington; Clayton L. Calkin, both of Houston, Tex.

[73] Assignee: Shell Oil Company, Houston, Tex.

[21] Appl. No.: 35,111

[22] Filed: Apr. 6, 1987

[51] Int. Cl.$^4$ .............................................. E21B 49/00
[52] U.S. Cl. ...................................................... 73/153
[58] Field of Search ..................... 73/153, 23.1; 436/31

[56] References Cited

U.S. PATENT DOCUMENTS

| | | | |
|---|---|---|---|
| 2,095,056 | 10/1937 | Clough | 73/153 X |
| 2,320,681 | 6/1943 | Thompson | 73/153 |
| 2,379,045 | 6/1945 | Sturgis | 73/153 X |

OTHER PUBLICATIONS

Hawley, The Condensed Chemical Dictionary, 8th ed. Van Nostrand, N.Y. 1971, pp. 255, 368 and 402.
Dowdco Sponge Coring, Brochure, Midland, Texas, pp. 1-8, 1981.

Primary Examiner—Jerry W. Myracle

[57] ABSTRACT

A method for quantifying the volume of oil in the fluids produced by solvent extracted sponge core distills only a portion of the solvent from the solvent/oil mixture, then determines and subtracts the remaining solvent volume to yield the actual volume of oil removed from the sponge.

7 Claims, 3 Drawing Sheets

QUANTITATION OF OIL IN SPONGE CORE EXTRACTS

METHOD FOR ANALYZING SOLVENT EXTRACTED SPONGE CORE

CROSS REFERENCE TO RELATED APPLICATIONS

Reference is made to copending U.S. patent application Ser. No. 814,334, filed Dec. 27, 1985, the disclosure of which is incorporated herein by reference, and to U.S. patent application Ser. No. 035,110, filed contemporaneously herewith, both of which are assigned to the assignee of the present application.

BACKGROUND OF THE INVENTION

The present invention relates to the exploration and production of petroleum from earth formations, and more particularly to methods for determining the amount of oil present in such a formation.

In the petroleum industry, one of the most valuable and informative tecnhiques for determining the characteristics of an earth formation located well below the surface, and the nature of the fluids which it may contain, is to remove and bring a portion of the formation to the surface for analysis. This is most commonly done by "coring" the formation. Of curse, physical conditions in the formation are substantially different from those at the surface: pressures and temperatures are ordinarily enormously elevated over surface conditions. Therefore, fluids and gases present in porous rock samples very often evolve from those samples as they are recovered from the formation. To the extent that such liquids and gases are lost, the accuracy of the evaluation of the formation production potential is accordingly impaired.

To control this problem, a technique calle "pressure coring" is often employed. With pressure coring, the core is contained at substantially its original formation pressure until proper analysis can be made. Pressure coring, while overcoming fluid loss problems to a great extent, is quite expensive.

A recently developed alternative technique, "sponge coring", shows typical savings of around 70 percent of the cost of pressure coring after considering the savings in both the cutting of the core from the formation and the subsequent analysis of the core. In sponge coring, as the core is cut, it enters a typically half-inch thick polyurethane sponge liner inside the inner core barrel. As the core is brought to the surface, the sponge then captures any formation fluids that escape from the core when the pore preesure drops below the oil's bubble point. Such expanding gas bubbles can displace otherwise immobile oil, and any such oil which bleeds from the core (and this can be as much as 50% of the original core fluid) is thus caught and retained by the sponge liner. An analysis is then made of the oil captured by the sponge, and by adding that to the amount left in the core, one can obtain much more accurate oil saturation values for the formations from which the core was removed.

The importance of coring in the production of petroleum has recently been increasing as more and more secondary and tertiary recovery is being made of petroleum reserves. In a formation undergoing primary production, the original reservoir fluids are little altered from their condition for the last serveral thousand years. They may migrate as the oil is produced, but their properties are little changes. However, when fluids and/or other compounds are injected into a formation to stimulate its production, the nature of the connate fluids is accordingly altered, sometimes to a very substantial extent. When this occurs, the more traditional wellbore logging tools may be unable to provide further useful information. In all too many instances, the only way to determine how much oil is left, and thus whether it can be produced economically, is to go down to the formation and take a core sample.

It will therefore be appeciated that the analysis of the oil content of the core sample can be critically important. The final true residual oil saturation of a formation is a determination that can make or break a multi-million dollary enhanced recovery project.

As explained in greater detail in the aboe-referenced '334 application, a major disadvantage of sponge coring has been the inability to accurately measure the amount of oil retained by the sponge. Many techniques for oil determination have been used by service companies, including mechanical extraction, retorting, and solvent extraction. The problems with these techniques, as they are presently practiced, include incomplete extraction of oil, mistaking extracted sponge components for oil, and in the case of solvent extraction, incomplete removal of extracting solvent before measuring oil volume.

The above-referenced '334 application discloses a substantial improvement in determining the amount of oil in a sponge core. Several solvents are identified which have the unique capacity, previously unrecognized in this industry, to remove substantially all of the oil captured by the sponge without affecting the sponge or dissolving (usually unreacted) sponge components. Highly accurate determination of the oil captured in the sponge is thus made possible, thereby effectively realizing the enormous savings potential of sponge core technology.

There does remain a need, however, to be able to practice this substantial improvement in an efficient and commercially practical manner such that substantial quantities of sponge core (often several hundred feed of core in a typical coring operation) can be analyzed quickly and efficiently. For example, when sponge core is manufactured, the sponge is foamed in place inside an aluminum liner. The sponge then bonds fairly well to the aluminum, making removal of the sponge from the liner difficult and time consuming. In analyzing the sponge core, it would therefore be preferable to analyze it in place in the liner barrel.

A need thus remains for a convenient, effective, and commercially practical method and apparatus for removing the captured oil from the sponge, preferably without having to remove the sponge from the aluminum liner. A need also remains for a method for accurately analyzing the actual amount of oil removed when solvents such as the Freon-11 identified in the above-referenced '334 application are used. Typically, a large amount of solvent is used, resulting in a highly diluted solution, since there is usually not much oil present. Removing the solvent in order to improve the accuracy of the determination of the oil is not as easy as simply evaporating the solvent because the light (e.g., $C_5$–$C_8$) hydrocarbons from the captured formation oil will usually also evaporate.

SUMMARY OF THE INVENTION

Briefly, the present invention meets the above needs and purposes by providing a large size solvent extraction device in which lengths of the aluminum liner (typically one foot) with sponge intact therein can be placed for solvent extraction. A unique solvent disperser assures that the solvent will be distributed and applied to the sponge. After the oil has been removed from the sponge, a unique distillation method and analytical procedure are provided which accurately determine the volume of oil removed from the sponge, including the light hydrocarbons.

More particularly, large Soxhlet extractors are furnished in which one-foot sections of the aluminum liner, with sponge intact therein, are located. The solvent is refluxed in conventional manner through the Soxhlet extractor. However, the refluxed solvent in such an extractor ordinarily drips down the center and would miss the sponge, since the sponge core lines the inner wall of the aluminum cylinder and is hollow in the center. Therefore, to prevent the solvent from merely dripping down the hollow center of the cylinder without contacting the sponge, the present invention provides a unique solvent disperser especially adapted for use in determining the oil captured by the sponge core.

In particular, the disperser includes a body which is capable of conducting liquid solvent therein, e.g., by capillary and/or gravitational action. The body includes a region, defining an application zone, which matches the dimensions of the sponge for conducting solvent to the sponge and passing it to the sponge. The solvent disperser body also includes a region for receiving solvent which is dripping downwardly within the Soxhlet extractor and dispersing the solvent by conducting it to the application zone, whence it is delivered to the sponge.

Once the oil has been removed from the sponge, it is then analyzed by first distilling but a portion of the solvent from the solvent/oil mixture. Thus, in such a solvent extracted sponge core measurement process, the solvent/oil mixture is first separated from the water in the extracted fluids. Next, the mixture is carefully distilled to remove a portion of the solvent from the solvent/oil mixture substantially without co-distillation or loss of the light hydrocarbons in the mixture. Typically, with Freon-11 solvent, the solvent can be removed until the remaining solution contains less than 15% Freon-11, without significant loss or co-distillation of the light hydrocarbons. A determination of the solvent remaining in the mixture is then made, following which the actual volume of oil removed from the sponge is then determined by subtracting the determined remaining solvent volume.

In a preferred embodiment of the invention the dispenser is a disc shaped capillary body made from a sheet of sintered stainless steel and having several vents formed therein for permitting vapor to pass therethrough. The capillaries in the sintered stainless steel body define solvent conduits for conducting solvent liquid within the body. On the outward rim of the body is an application zone which is dimensioned for contacting the sponge in a sponge core barrel for receiving solvent from the capillary conducting means within the sintered stainless steel body and passing the solvent to the sponge. The underside of the body outside the application zone has a burnished surface in order to substantially close the pores of the underside of the body to help retain solvent within those portions of the body which are distant from the sponge. In the center of the body is a raised hub for receiving the solvent dripping down from the extractor and dispersing the solvent outwardly to the application zone, the hub being raised and located above the rest of the body to gravitationally assist the solvent in flowing away thereform.

In the preferred embodiment of the invention, Freon-11 solvent is used for extracting the oil from the sponge core. The preferred method for quantifying the volume of oil in the fluids resulting from such extraction then proceeds by first separating the solvent/oil mixtures from the water in the extracted fluids. Next, a Vigoreaux fractional distillation reflux column surmounted with a column condenser is then employed to distill at least a portion of the solvent from the solvent/oil mixture. With this method, the solvent portion si distilled without substantial co-distillation or loss of the light $C_5$–$C_8$ hydrocarbons in the mixture. This is accomplished by gradually distilling until a vapor temperature limit of substantially 65° Celsius is reached in the solvent/oil mixture. At that point, distillation is discontinued.

Even though the Freon-11 solvent removes very little of the polyurethane sponge core material, there will nevertheless be some extracted sponge components in the resulting solvent/oil mixture. This is believed to be due in large part to chemical degradation of the sponge resulting from prior exposure to borehole conditions such as elevated temperature, hydrogen sulfide, and the solvent action of the formation fluids themselves. These extracted sponge components are then removed from the solvent/oil mixture by centrifugation. Next, the amount of solvent remaining in the mixture is determined utilizing gas chromatography, and the volume of oil actually removed from the sponge is then finally determined by subtracting from the volume of the mixture the volume of the solvent which was thus determined. Typically, the volume of Freon-11 remaining will be less than 15%.

It is therefore an object of the present invention to provide a substantially improved method for determining the amount of oil in a sponge core; such a method which is particularly well adapted for use in solvent extracted sponge core measurements for quantifying the volume of oil in the fluids resulting from such extractions; in which the water in such extracted fluids is first separated from the solvent/oil mixture thereof; in which at least a portion of the solvent from the solvent/oil mixture is then distilled away from the mixture substantially without co-distillation or loss of the light hydrocarbons in the mixture; in which the volume contribution of the solvent remaining in the mixture is then determined; in which the volume of oil removed from the sponge is then determined by substracting the determined remaining solvent volume; and to accomplish the above objects and purposes in an inexpensive, uncomplicated, versatile, economical and reliable method readily suited to the widest possible utilization in the analysis of oil-bearing earth formations by sponge coring methods.

These and other objects and advantages of the invention will be apparent from the following description, the accompanying drawing, and the appended claims.

DESCRIPTION OF THE PREFERRED EMBODIMENT

Figure 1:
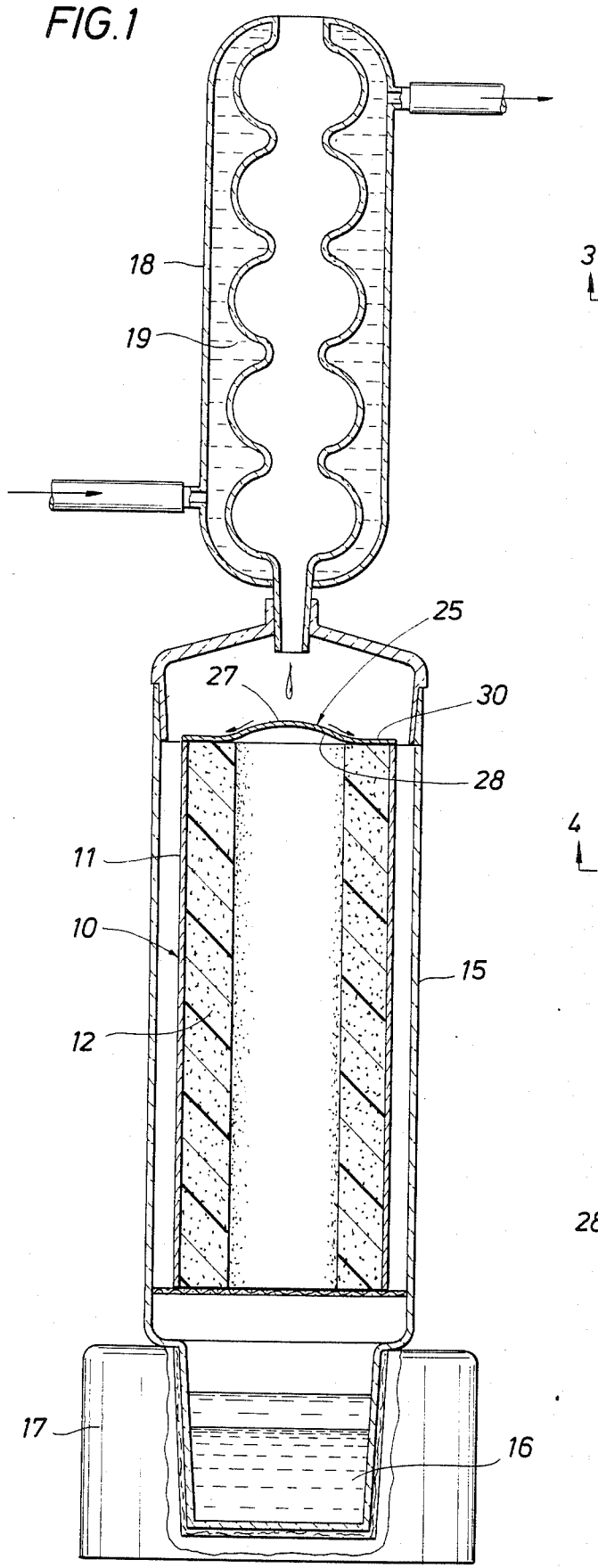
FIG. 1 is a fragmentary cross-sectional view of a Soxhlet extration apparatus and system for solvent removal of the oil from the sponge core.
Figure 2:
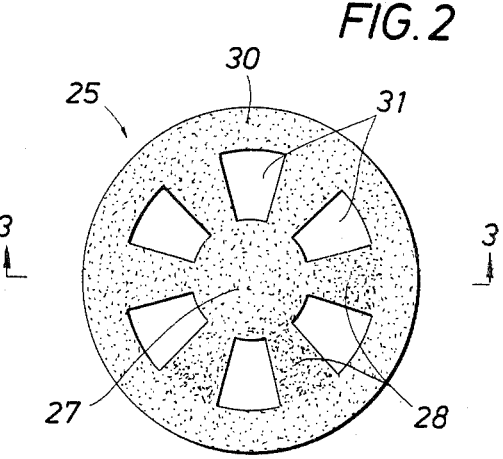
FIG. 2 is a plan view of the disperser employed in the system shown in FIG. 1.
Figure 3:
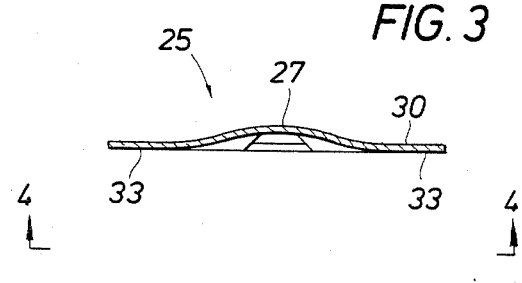
FIG. 3 is a cross-sectional view of the disperser shown in FIG. 2, taken on line 3—3 thereof.
Figure 4:
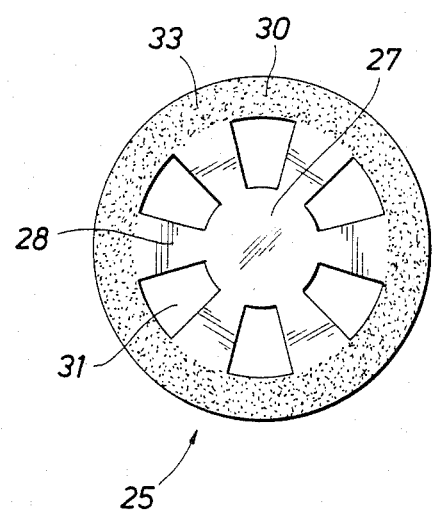
FIG. 4 is a bottom view of the disperser taken on view line 4—4 in FIG. 3.

With reference to the drawings, the new and improved method and apparatus for use in determining the oil saturation of an earth formation by means of sponge coring will be described. The sponge core and liner are left intact, and cut into lengths of convenient size, such as one-foot sections 10 (FIG. 1). The section 10 then consists of the aluminum barrel 11 and the polyurethane sponge 12 lining the inside thereof. The center of the section 10, as can be seen, is hollow, having previously received the formation core sample therein.

The section is then placed in an oversized Soxhlet extractor 15 of sufficient size to receive a section 10. The solvent 16 in the bottom of the extractor 15 is heated at the bottom by a heater 17 causing solvent vapors to rise and be condensed in an Allihn condenser 18, cooled by coolant 19. The solvent then drips back down so that it can percolate through the sponge for removing the formation fluids therefrom. In the preferred embodiment, the reflux rate of the solvent was equal to approximately one to two times the pore volume of the sponge per hour, and the process was continued for approximately 48 hours. Due to the low boiling point of the Freon-11 solvent (23.8° C., the coolant 19 is refrigerated, preferably around ice-water temperatures (e.g., using a water-ethylene glycol coolant at 3° C.).

In order to assure proper dispersion of the recirculating solvent 16, which drips down through the center of the Soxhlet extractor 15 from the condenser 18, a solvent disperser 25 is located on top of the liner/sponge section 10. Disperser 25, in the preferred embodiment, is a disc shaped capillary body made from a sheet of sintered stainless steel. Formed in the shape of a spoked wheel, the disperser 25 has a central hub 27 from which a series of spokes 28 radiate to an outer rim 30. The openings 31 between the rim and spokes provide vents 31 for the solvent vapor to rise to the condenser 18. The sintered stainless steel is thus a porous capillary body which readily conducts the solvent as it drips downwardly onto the hub 27. As can be seen from the drawings, the hub 27 is raised and located above the rest of the disperser body 25 so that the flow of the solvent away from hub 27 is further assisted by gravity.

The bottom of the rim 30 constitutes an application zone 33 which, as can be seen, is dimensioned for contacting the sponge 12 in the sponge core barrel 11. The rim 30 thus receives solvent from the capillaries within the disperser 25 and passes the solvent on to the sponge 12.

The underside of the hub 27 and spokes 28 of disperser 25 is burnished to close the pores of the disperser body 25 on the underside thereof in those areas outside the application zone 33 on the underside of the rim 30. This discourages the solvent from dripping off the disperser 25 outside the application zone, thus helping to retain solvent within those portions of the disperser body 25 which are distant from the sponge 12.

At this point, the fluid mixture is highly diluted with solvent. In order to accurately quantify the extracted volume of oil, it is therefore desirable to remove the solvent therefrom. According to the preferred embodiment of the invention, it has been discovered that it is preferable, in order to retain the light hydrocarbons, not to remove all of the solvent. Rather, the majority of the solvent is removed and then the volume of the remaining solvent is determined.

Figure 5:
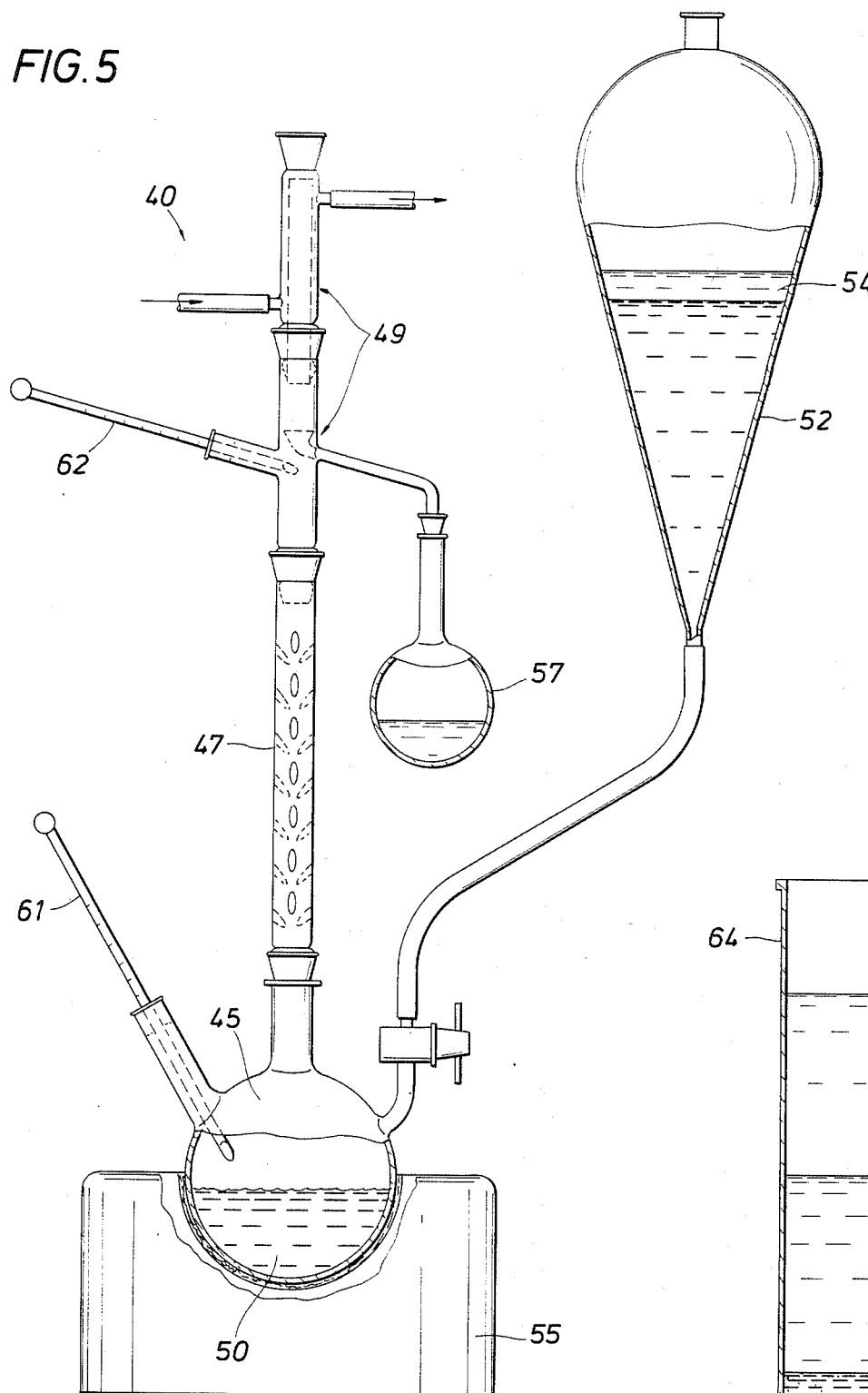
FIG. 5 is a fragmentary partially sectioned view of the solvent extraction apparatus and system for removing most of the solvent from the solvent/oil mixture.
Figure 6:
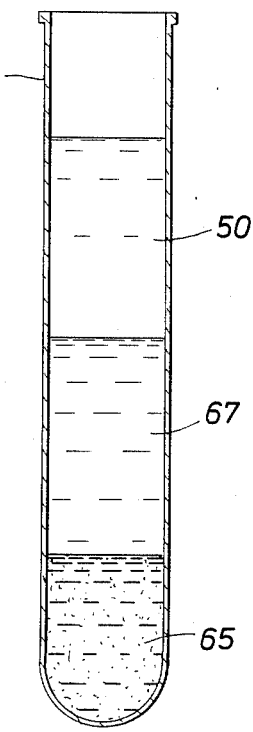
FIG. 6 is a cross-sectional view of a measuring tube used for measuring the final volume of the concentrated solvent/oil mixture.
Figure 7:
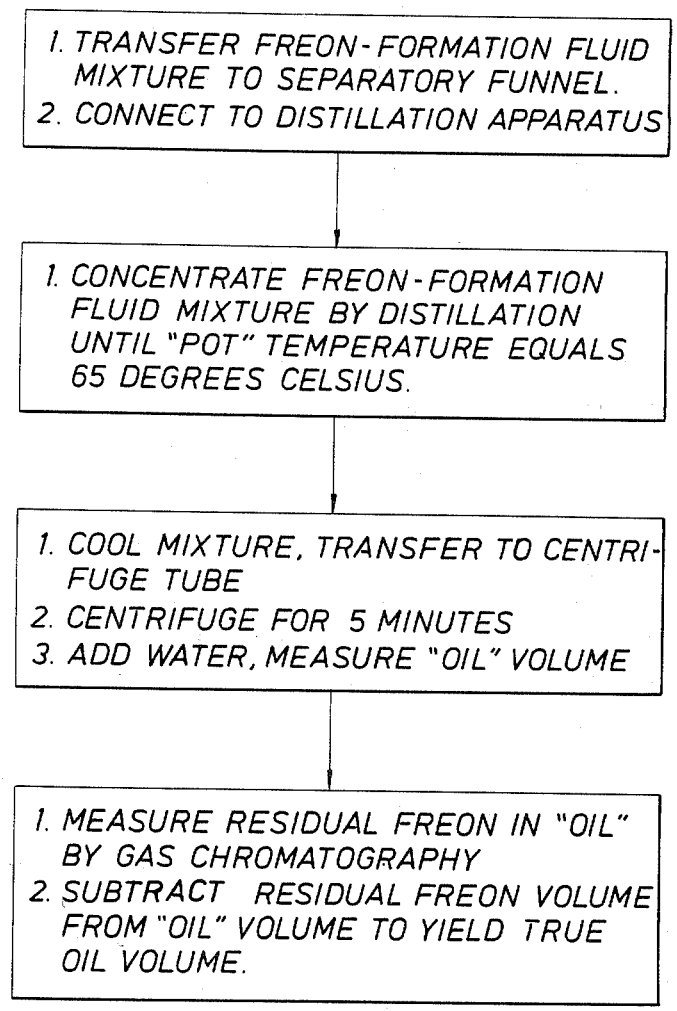
FIG. 7 is a flow chart illustrating the steps performed in quantitation of the oil in the sponge core solvent/oil extracts.

To accomplish this, the solvent extraction apparatus 40 illustrated in FIG. 5 was employed, consisting of a 100 ml round bottom flask 45, Vigoreaux fractional distillation column 47, and a condenser assembly 49. The distillation column 47, operating at ambient room temperature, thus provides a dynamic separation of the solvent from the solvent/oil mixture 50. By employing active distillation in this fashion, rather than simply trying to evaporate the solvent from the mixture, loss of the light hydrocarbons from the mixture 50 is effectively curtailed.

Prior to introducing the solvent/oil mixture 50 into the flask 45, it is placed in a separatory funnel 52, where the water 54 is allowed to rise above the solvent/oil mixture. In this way, the water in the extracted fluids is separated from the solvent/oil mixture before introduction into the flask 45. As space then becomes available within flask 45, during distillation (aided by heater 55), additional amounts of the solvent/oil mixture are introduced, over time, from the separatory funnel 52, until all of the solvent/oil mixture is in the flask 45. Distillation of the mixture in flask 45 proceeds, in the preferred embodiment, until the vapor temperature reaches approximately 65° C., at which time heating is discontinued and the mixture is allowed to cool. Typically, the solvent/oil mixture in flashk50 can be concentrated, without significant loss of light ends, by distillation, until the remaining solution contains less than 15% Freon-11. The distilled Freon-11 is collected in flask 57. Temperatures may be conveniently monitored by thermometers 61 and 62.

Next, the concentrated solvent/oil mixture is centrifuged in a centrifuge tube 64 to separate and remove the extracted sponge components 65 from the solvent/oil mixture 50, and the residual Freon in the solvent/oil mixture is measured by standard gas chromatography (not shown). From these measurements the volume contribution of the solvent remaining in the mixture is readily determined, and can be subtracted, thereby yielding the volume of the oil actually removed from the sponge. These measurements can be conveniently made using a centrifuge tube 64 having a volume calibration scale on the side thereof, and by adding a quantity of water 67 sufficient to more visibly separate the sponge material 65 from the solvent/oil mixture. Water will usually have an intermediate density, or a base can be added to adjust the density as appropriate.

In measuring the residual solvent by gas chromatography, standard procedures are followed, in which oil-solvent standard solutions on a volume-to-volume basis are used. Due to the high volatility of the Freon-11 used in the preferred embodiment, it has been considered more accurate to prepare the standard solutions on a weight-to-weight basis and then convert them to a volume-to-volume basis. This was done by injecting a known weight of Freon into a vial sealed with a mininert valve containing the known weight of oil. The type of standard thus obtained is a weight-to-weight ratio. Conversion to a volume-to-volume ratio is done by a determination of the densities of the Freon and oil. The respective component volumes are then calculated for a volume-to-volume standard to be consistent with the use of constant volume aliquots of unknowns.

As may be seen, therefore, the present invention has numerous advantages. Principally, it provides a very convenient, efficient, and cost effective method and apparatus for accurately determining the oil saturation of an earth formation by means of sponge coring. The sponge can be left intact in the metal barrel in which it is usually formed and to which it is usually tightly adhered. The solvent is efficiently refluxed through the sponge for extracting all of the oil from the sponge. The volume of oil removed from the sponge is then accurately determined with little if any loss of the light hydrocarbons therefrom. The technique is robust, yielding consistent results over very wide ranges, such as, for example, 19°–43° gravity oil. The invention is thus highly versatile, efficient, accurate, reliable, and readily suited to the widest utilization in the analysis of oil-bearing earth formations by sponge coring methods.

While the methods and apparatus herein described constitute preferred embodiments of this invention, it is to be understood that the invention is not limited to these precise methods and apparatus, and that changes may be made therein without departing from the scope of the invention.

What is claimed is:

1. For use in solvent extracted sponge core measurements of the oil saturation of earth formations, a method for quantifying the volume of oil in the fluids resulting from such extraction, comprising:
    (a) separating the solvent/oil mixture from the water in the extracted fluids,
    (b) distilling at least a portion of the solvent from the solvent/oil mixture substantially without co-distillation or loss of the light hydrocarbons in the mixture,
    (c) determining the volume contribution of the solvent remaining in the mixture, and
    (d) determining the volume of oil removed from the sponge by substracting the determined remaining solvent volume.

2. The method of claim 1 further comprising removing extracted sponge components from the solvent/oil mixture.

3. The method of claim 2 wherein said step of removing extracted sponge components from the solvent/oil mixture further comprises removing the extracted sponge components by centrifugation.

4. The method of claim 1 wherein said step of determining the volume contribution of the solvent remaining in the mixture further comprises determining the volume contribution utilizing gas chromatography.

5. The method of claim 1 wherein said step of distilling at least a portion of the solvent from the solvent/oil mixture further comprises distilling with a Vigoreauz fractional distillation reflux column.

6. For use in Freon-11 solvent extracted sponge core measurements of the oil saturation of earth formations, a method for quantifying the volume of oil in the fluids resulting from such extraction, comprising:
    (a) separating the solvent/oil mixture from the water in the extracted fluids,
    (b) distilling at least a portion of the solvent from the solvent/oil mixture substantially without co-distillation or loss of the light $C_5$–$C_8$ hydrocarbons in the mixture, by distilling to a vapor temperature limit of substantially 65° C. using a Vigoreaux fractional distillation reflux column surmounted with a column condenser.
    (c) removing extracted sponge components from the solvent/ oil mixture by centrifugation,
    (d) determining the volume contribution of the solvent remaining in the mixture utilizing gas chromatography, and
    (e) determining the volume of oil removed from the sponge by subtracting the determined remaining solvent volume.

7. The method of claim 6 wherein said distilling step further comprises concentrating the original solvent/oil mixture to contain less than substantially 15% Freon-11.

* * * * *